(12) United States Patent
Beynon et al.

(10) Patent No.: US 8,399,402 B2
(45) Date of Patent: Mar. 19, 2013

(54) POLYPEPTIDE AS STANDARD FOR PROTEOME ANALYSIS

(75) Inventors: Robert Beynon, Merseyside (GB); Simon Gaskell, Cheshire (GB); Julie Pratt, Leicester (GB); Claire Eyers, Manchester (GB)

(73) Assignee: Polyquant GmbH, Bad Abbach (DE)

( * ) Notice: Subject to any disclaimer, the term of this patent is extended or adjusted under 35 U.S.C. 154(b) by 387 days.

(21) Appl. No.: 12/599,960

(22) PCT Filed: Apr. 15, 2008

(86) PCT No.: PCT/EP2008/002988
§ 371 (c)(1),
(2), (4) Date: Apr. 1, 2010

(87) PCT Pub. No.: WO2008/128679
PCT Pub. Date: Oct. 30, 2008

(65) Prior Publication Data
US 2010/0197889 A1    Aug. 5, 2010

(30) Foreign Application Priority Data
Apr. 19, 2007    (EP) .................................... 07008003

(51) Int. Cl.
*A61K 38/00*    (2006.01)
(52) U.S. Cl. ....................................................... 514/1.1
(58) Field of Classification Search .................. None
See application file for complete search history.

(56) References Cited

U.S. PATENT DOCUMENTS
2007/0048752 A1 *  3/2007  Yan et al. ........................ 435/6

OTHER PUBLICATIONS

Eyers et al. QCAL—a Novel Standard for Assessing Instrument Conditions for Proteome Analysis. JASMS, Jul. 2, 2008 published online. vol. 19, No. 9, pp. 1275-1280.*

Beynon, et al., "Multiplexed absolute quantification in proteins using artificial QCAT proteins of concatenated signature peptides", British J. Pharmacology, 2 (8):587-89 (2005).
Brancia, and Gaskell, "Improved matrix-assisted laser desorption/ionization mass spectromettic analysis of tryptic hydrolysates of proteins following guanidination of lysine-containing peptides", Rap. Comm. Mass. Spectrom, 14:2070-73 (2000).
Cottrell, "Protein identification by peptide mass fingerprinting", Pept. Res., 7:115-24 (1994) Abstract Only.
Pratt, et al., "Multiplexed absolute quantification for proteomics using concatenated signature peptides encoded by QconCAT genes", Natl. Protocols., 1:1029-43 (2006).
Song, et al., "Effect of pH\ on the rate of asparagine deamidation in polymeric formulations:\pH\-rate profile", J. Pharm. Sci., 90:141-56 (2001).
Sun, et al., "A systematical analysis of tryptic peptide identification with reverse phase liquid chromatography and electrospray ion trap mass spectrometry". Genomics Prot. Bioinfo., 2:174-83 (2002) Abstract Only.
Washburn, et al., "Large-scale analysis of the yeast proteome by multidimensional protein identification technology", Natl. Biotechnol., 19:242-47 (2001).
ISR PCT/EP2008/002988 mailed Aug. 14, 2008.
ESR EP07 008 003 mailed Oct. 9, 2007.
First EPO Office Action dated Jun. 24, 2008.
Second EPO oOffice Action dated Oct. 5, 2009.

* cited by examiner

*Primary Examiner* — Marcela M Cordero Garcia
(74) *Attorney, Agent, or Firm* — Pabst Patent Group LLP

(57) ABSTRACT

The present invention provides a polypeptide as standard for peptide analysis by mass spectrometry comprising at least 16 peptides selected from the group consisting of the peptides of SEQ ID NO: 1 to SEQ ID NO: 22 or variants thereof, together with an artificial protein comprising the polypeptide, a vector comprising a nucleic acid encoding the polypeptide, a kit for proteome analysis, a selection of peptides for calibration an devaluation of mass spectrometers and chromatographs for proteome analysis and uses thereof.

9 Claims, 5 Drawing Sheets

| Q-peptide | Sequence | [M+H]⁺ | [M+2H]²⁺ |
|---|---|---|---|
| SEQ ID NO: 1 | VFDEFKPLVEEPQNLIR | 2073.1021 | 1037.0550 |
| SEQ ID NO: 2 | VFDEFKPLVKPEEPQNLIR | 2298.2498 | 1149.6289 |
| SEQ ID NO: 3 | VFDEFKPLVKPEEKPQNLIR | 2426.3448 | 1213.6763 |
| SEQ ID NO: 4 | VFDEFKPLVKPEEKPQNKPLIR | 2651.4925 | 1326.2502 |
| SEQ ID NO: 5 | VFKPDEFKPLVKPEEKPQNKPLIR | 2876.6403 | 1438.8241 |
| SEQ ID NO: 6 | VFKPDEFKPLVKPEEKPQNKPLIKPR | 3101.7880 | 1551.3979 |
| SEQ ID NO: 7 | VFDEFQPLVEEPQNLIR | 2073.0657 | 1037.0368 |
| SEQ ID NO: 8 | GVNDNEEGFFSAR | 1441.6348 | 721.3214 |
| SEQ ID NO: 9 | GGVNDNEEGFFSAR[a] | 1498.6563 | 749.8321 |
| SEQ ID NO: 10 | GGGVNDNEEGFFSAR[b] | 1555.6778 | 778.3428 |
| SEQ ID NO: 11 | GVNDNEEGFFSAK | 1413.6287 | 707.3183 |
| SEQ ID NO: 12 | AVMDDFAAFVEK | 1342.6354 | 671.8216 |
| SEQ ID NO: 13 | AVMMDDFAAFVEK | 1473.6758 | 737.3419 |
| SEQ ID NO: 14 | AVMMMDDFAAFVEK | 1604.7163 | 802.8621 |
| SEQ ID NO: 15 | GLVK | 416.2873 | 208.6476 |
| SEQ ID NO: 16 | FVVPR | 617.3776 | 309.1927 |
| SEQ ID NO: 17 | ALELFR | 748.4358 | 374.7218 |
| SEQ ID NO: 18 | IGDYAGIK | 836.4518 | 418.7299 |
| SEQ ID NO: 19 | EALDFFAR | 968.4842 | 484.7460 |
| SEQ ID NO: 20 | YLGYLEQLLR | 1267.7051 | 634.3565 |
| SEQ ID NO: 21 | VLYPNDNFFEGK | 1442.6957 | 721.8518 |
| SEQ ID NO: 22 | LFTFHADICTLPDTEK | 1850.8999 | 925.9539 |

Figure 1 A

POLYPEPTIDE AS STANDARD FOR PROTEOME ANALYSIS

REFERENCE TO SEQUENCE LISTING

The Sequence Listing submitted Nov. 2, 2012 as a text file named "PTR_4_8401_AMD_AFD_Sequence_Listing.txt," created on Nov. 2, 2012, and having a size of 5,936 bytes is hereby incorporated by reference pursuant to 37 C.F.R. §1.52(e)(5).

FIELD OF THE INVENTION

The present invention relates to the field of proteomics, in particular to the quantification of proteins and to polypeptide standards to optimise the separation of peptides by reversed-phase chromatography and their detection and fragmentation by mass spectrometry.

The present invention therefore provides a polypeptide as standard for peptide analysis by mass spectrometry which comprises at least 16 peptides, preferably 18 peptides, more preferably 20 peptides, most preferably 22 peptides selected from the group consisting of the peptides of SEQ ID NO: 1 to SEQ ID NO: 22 and/or functional variants thereof. The invention is further directed to an artificial protein comprising such a polypeptide and a vector comprising a nucleic acid encoding the polypeptide and/or the artificial protein. Additionally, the invention encompasses a kit for proteome analysis, a selection of peptides for calibration and evaluation of mass spectrometers and chromatographs for proteome analyses and the use of the peptides according to the invention for calibration and evaluation of mass spectrometers and chromatographs for proteome analyses.

BACKGROUND OF THE INVENTION

With the ever increasing number of published manuscripts reporting peptide characterisation by reversed-phase chromatography coupled with mass spectrometric analysis, there is a pressing need to precisely define the instrument conditions used for these analyses. At present, instrument calibration and optimisation is performed on a laboratory-by laboratory basis, with no two facilities using the same criteria for instrument set-up. Many laboratories using multiple mass spectrometers for analysis of the same sample also use different standards for calibration and optimisation of the different instruments. In addition, the chromatographic conditions like solvents, solid-phase and elution gradient used for separation of peptides by reverse-phase are seldom the same. This makes both intra- and inter-laboratory comparisons of proteomics data almost impossible to perform with any degree of consistency.

EP 1 736 480 A1, Beynon et al., 2005 and Pratt et al., 2006 describe a Qcon-CAT methodology for the construction of tryptic peptide sequences but do not disclose a single polypeptide standard for optimising separation of peptides by reversed-phase chromatography and their detection and fragmentation by mass spectrometry, in addition to maintaining reproducibility in proteomics experiments, which requires that instrument parameters be optimised and standardised according to defined criteria. No single standard currently exists which can be used to assess instrument performance in this manner.

Thus there is still an existing need for such a single polypeptide standard.

SUMMARY OF THE INVENTION

The present invention therefore provides a polypeptide as standard for peptide analysis by mass spectrometry which comprises at least 16 peptides, preferably 18 peptides, more preferably 20 peptides, most preferably 22 peptides selected from the group consisting of the peptides of SEQ ID NO: 1 to SEQ ID NO: 22 and/or functional variants thereof. The invention is further directed to an artificial protein comprising such a polypeptide and a vector comprising a nucleic acid encoding the polypeptide and/or the artificial protein. Additionally, the invention encompasses a kit for proteome analysis, a selection of peptides for calibration and evaluation of mass spectrometers and chromatographs for proteome analyses and the use of the peptides according to the invention for calibration and evaluation of mass spectrometers and chromatographs for proteome analyses.

DESCRIPTION OF THE DRAWINGS

FIG. 1A: Unique Q-peptides were chosen to assess peptide separation by reversed-phase chromatography and for optimisation and calibration of a range of mass spectrometers. The sequences of each of these peptides was concatenated in silico and used to generate a QconCAT construct as described in the section "Examples". Listed are the monoisotopic masses of the $[M+H]^+$ and $[M+2H]^{2+}$ ions. Each peptide is present as single copy except $^a$Q9 with 3 copies and $^b$Q10 with 6 copies.

FIG. 1B: After expression in *E. coli* BL21 (DE3) cells and purification by affinity chromatography on a Ni-NTA column, QCAL was digested with trypsin and the peptides analysed by MALDI-ToF MS.

FIG. 1C: Digested QCAL was further analysed using an FT ICR MS.

FIG. 1D: Upper panel: A high-resolution FT ICR mass spectrum, distinguishing the doubly charged species of Q1 and Q7, a difference of 0.0182 Th is shown. Lower panel: Data was collected over a range of m/z 900-1500 which confirms that the resolution of this instrument is sufficient to readily detect peptide deamidation. In this case, deamidated Q9 is depicted.

FIG. 2A depicts the base peak chromatogram of eluted QCAL peptides.

FIG. 2B depicts the tandem MS spectra of Q10. The peptide sequence is SEQ ID NO:10.

FIG. 2C depicts MS spectra for the section of the LC gradient (34.8-35.8 min) over which peptides Q8, Q9, Q10 eluted is also shown. The area under the curve for the first 5 isotope peaks was used to calculate peptide response.

DETAILED DESCRIPTION OF THE INVENTION

This invention describes a tool, termed QCAL, designed specifically to optimise and define instrument conditions for peptide analysis by mass spectrometry in the absence or presence of upfront peptide separation by reversed-phase chromatography.

In a first aspect, the present invention is directed to a polypeptide as standard for peptide analysis by mass spectrometry which comprises at least 16 peptides, preferably 18 peptides, more preferably 20 peptides, most preferably 22 peptides selected from the group consisting of the peptides of SEQ ID NO: 1 to SEQ ID NO: 22 and/or functional variants thereof. The peptides of SEQ ID NO: 1 to SEQ ID NO: 22 are also termed Q1 to Q22.

The term "functional variant" or "functional variants" of a peptide sequence means that conservative amino acid substitutions, like acid (Asp and Glu) or basic amino acid (Asn and Gln) substitutions can be made on the present peptides. Also aromatic amino acids may be exchanged against each other.

In a preferred embodiment individual peptides of SEQ ID NO: 1 to SEQ ID NO: 22 can be present in more than one peptide copy.

In particular, the peptide of SEQ ID NO: 9 can be present in up to 5 copies, preferably up to 3 copies; most preferably in 3 copies and the peptide of SEQ ID NO: 10 can be present in up to 10 copies, preferably up to 6 copies, most preferably in 6 copies.

In a further aspect, the present invention provides an artificial protein comprising the aforementioned polypeptide.

An additional aspect of the invention is a vector comprising a nucleic acid encoding the aforementioned polypeptide and/or the artificial protein.

The invention further encompasses a kit for proteome analysis. The kit may comprise the aforementioned polypeptide as standard for peptide analysis by mass spectrometry, the aforementioned artificial protein and/or the aforementioned vector.

The invention is further directed to a selection of peptides for calibration and evaluation of mass spectrometers and chromatographs for proteome analysis. Therefore the use of an inventive protein or polypeptide for calibration and evaluation of mass spectrometers and chromatographs for proteome analyses is also encompassed.

Figure 1:
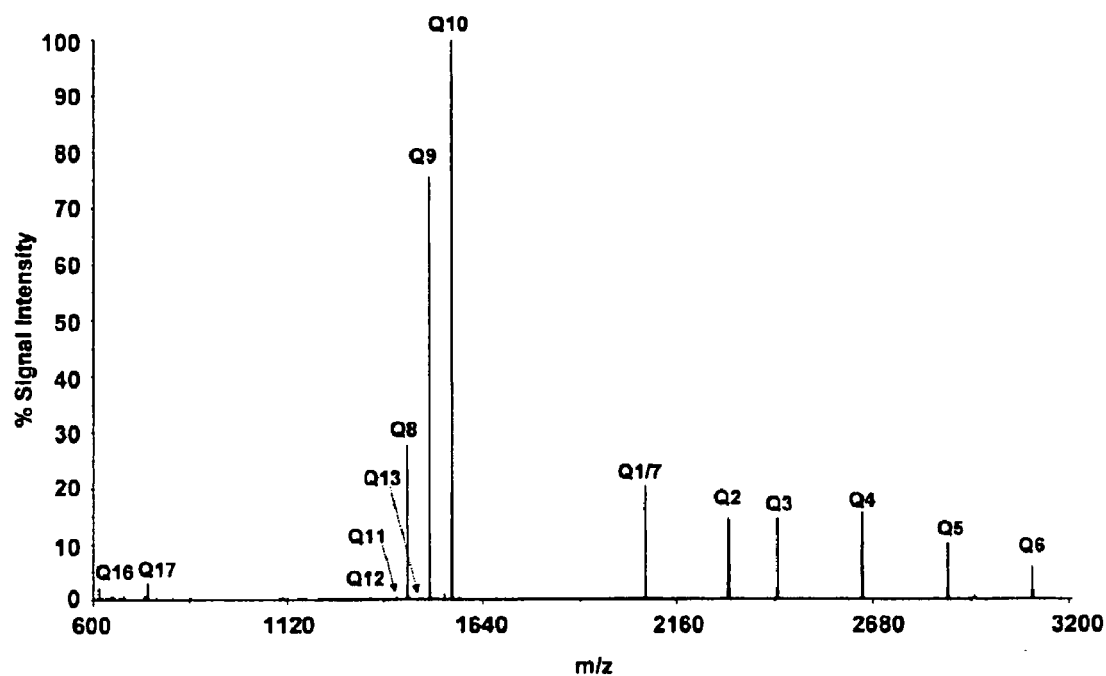
FIG. 1 shows design and implementation of the standard polypeptide QCAL.
Figure 1:
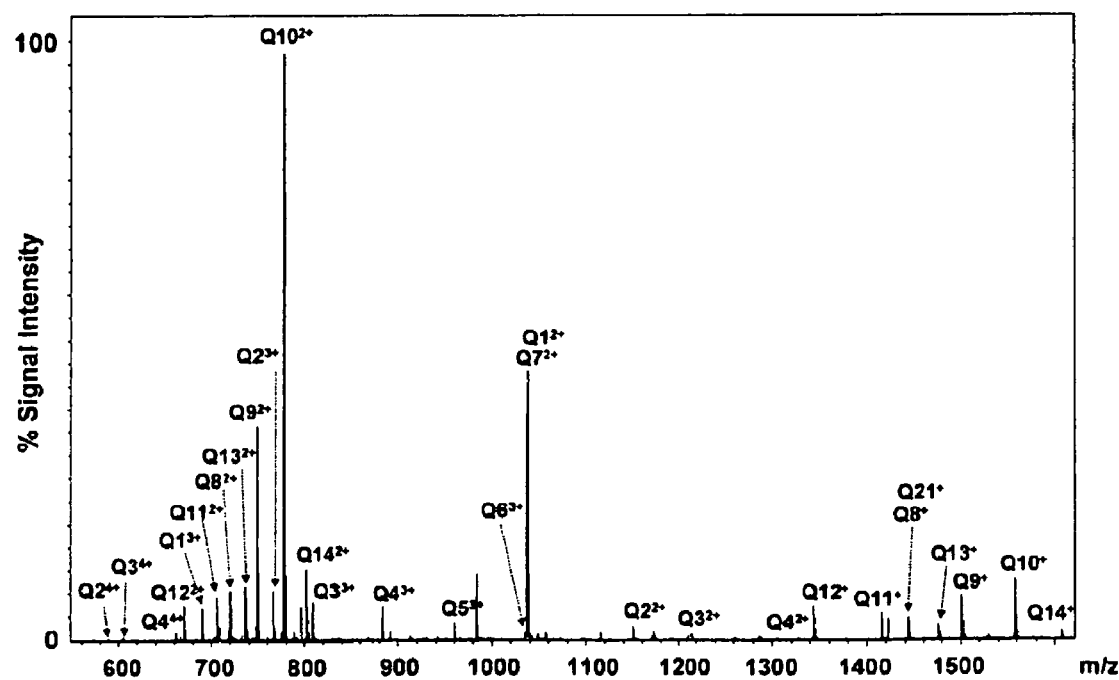
Figure 1:
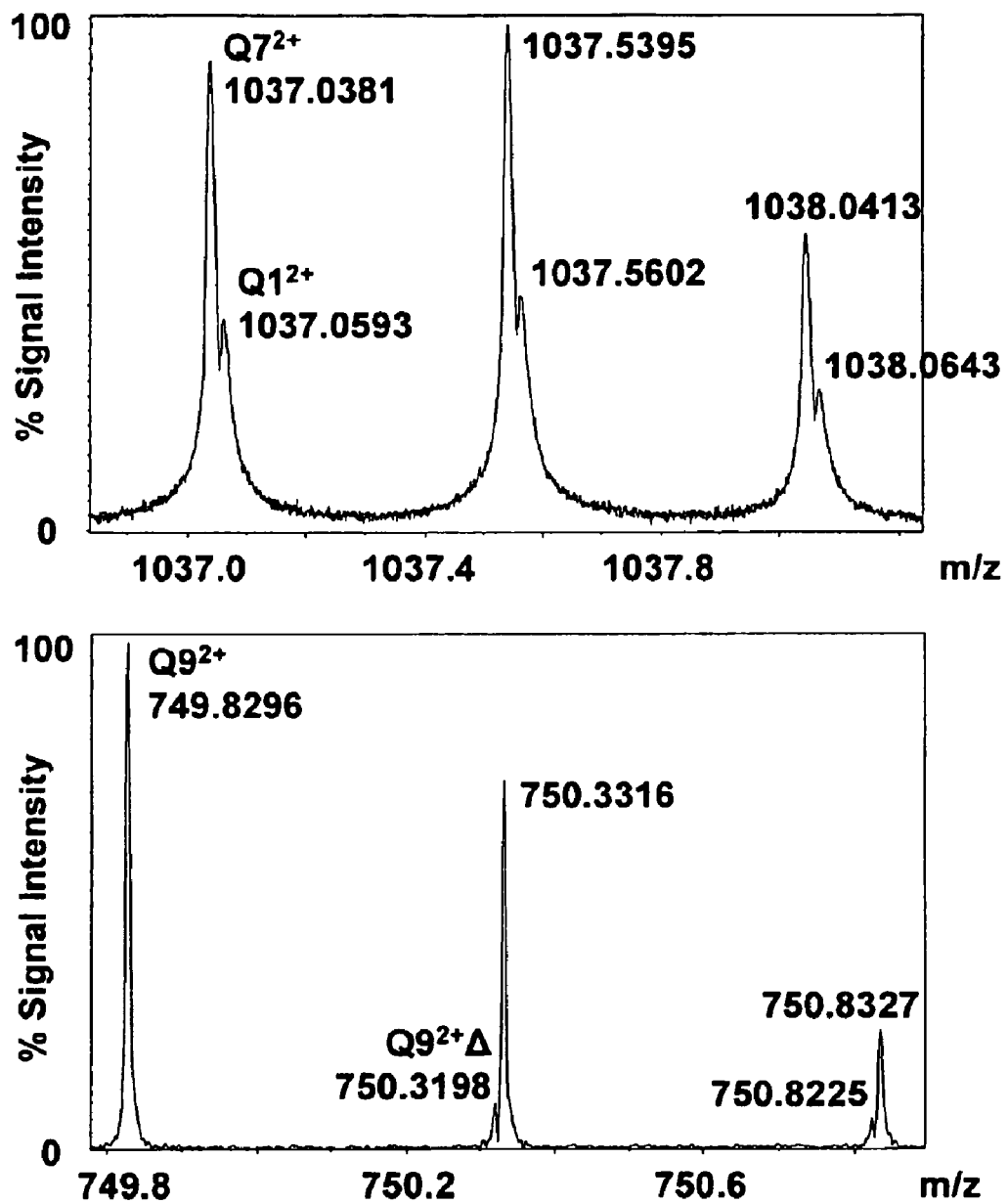

The artificial polypeptide, termed QCAL, was constructed using the QconCAT methodology and comprises 22 unique tryptic peptide sequences (SEQ ID NO: 1 to SEQ ID NO:22—FIG. 1A). The polypeptide is designed for calibration of a range of mass spectrometers typically used in peptide analysis.

In addition, the QCAL peptides were designed to facilitate the optimisation of instrument resolution, test the linearity of signal detection, as well as peptide separation by reversed-phase chromatography. Moreover, as these peptides are incorporated into an artificial protein, generation of these standards requires the end-user to validate sample preparation procedures such as tryptic digestion and desalting conditions. Characteristics are also incorporated within the design to assess peptide modification such as deamidation, methionine oxidation and modification of lysine residues, for example by guanidination.

Peptide mass fingerprinting (PMF) experiments are typically performed using a matrix-assisted laser-desorption ionisation (MALDI) time-of-flight (ToF) mass spectrometer (MS) for the identification of proteins following in-gel digestion with trypsin (Cottrell, 1994). The tryptic peptides that are generated under these conditions and subsequently used for database searching and protein identification are typically between m/z 500 and 3500. However, as calibration of MALDI-ToF instruments for peptide analysis is generally performed with a mixture of synthetic peptides, calibration is usually not performed lower than m/z 800-900, even though peptides in this region may enhance search algorithm scores and subsequent protein identification.

QCAL, was therefore designed to incorporate tryptic peptides with $[M+H]^+$ monoisotopic masses of m/z<500 and m/z>3000. Analysis of QCAL peptides by MALDI-ToF MS (FIG. 1B and Table 1 below) confirms that these peptides provide suitable scope for instrument calibration over the mass range required for PMF studies.

TABLE 1

Monoisotopic masses measured by MALDI-ToF MS of trypsin digested QCAL.

| Q-peptide | Sequence | Theoretical $[M + H]^+$ | Measured $[M + H]^+$ | Δppm |
|---|---|---|---|---|
| SEQ ID NO: 1 | VFDEFKPLVEEPQNLIR | 2073.1021 | 2072.9913 | −53.45 |
| SEQ ID NO: 2 | VFDEFKPLVKPEEPQNLIR | 2298.2498 | 2298.1500 | −43.44 |
| SEQ ID NO: 3 | VFDEFKPLVKPEEKPQNLIR | 2426.3448 | 2426.2551 | −36.97 |
| SEQ ID NO: 4 | VFDEFKPLVKPEEKPQNKPLIR | 2651.4925 | 2651.4009 | −34.55 |
| SEQ ID NO: 5 | VFKPDEFKPLVKPEEKPQNKPLIR | 2876.6403 | 2876.5580 | −28.59 |
| SEQ ID NO: 6 | VFKPDEFKPLVKPEEKPQNKPLIKPR | 3101.7880 | 3101.7332 | −17.66 |
| SEQ ID NO: 7 | VFDEFQPLVEEPQNLIR | 2073.0657 | N.D. | N.D. |
| SEQ ID NO: 8 | GVNDNEEGFFSAR | 1441.6348 | 1441.5444 | −62.73 |
| SEQ ID NO: 9 | GGVNDNEEGFFSAR[a] | 1498.6563 | 1498.5707 | −57.12 |
| SEQ ID NO: 10 | GGGVNDNEEGFFSAR[b] | 1555.6778 | 1555.6038 | −47.54 |
| SEQ ID NO: 11 | GVNDNEEGFFSAK | 1413.6287 | 1413.5381 | −64.08 |
| SEQ ID NO: 12 | AVMDDFAAFVEK | 1342.6354 | 1342.5354 | −74.45 |
| SEQ ID NO: 13 | AVMMDDFAAFVEK | 1473.6758 | 1473.6070 | −46.71 |

TABLE 1-continued

Monoisotopic masses measured by MALDI-ToF MS of trypsin digested QCAL.

| Q-peptide | Sequence | Theoretical [M + H]⁺ | Measured [M + H]⁺ | Δppm |
|---|---|---|---|---|
| SEQ ID NO: 14 | AVMMMDDFAAFVEK | 1604.7163 | N.D. | N.D. |
| SEQ ID NO: 15 | GLVK | 416.2873 | N.D. | N.D. |
| SEQ ID NO: 16 | FVVPR | 617.3776 | 617.3346 | −69.57 |
| SEQ ID NO: 17 | ALELFR | 748.4358 | 748.3755 | −80.55 |
| SEQ ID NO: 18 | IGDYAGIK | 836.4518 | N.D. | N.D. |
| SEQ ID NO: 19 | EALDFFAR | 968.4842 | N.D. | N.D. |
| SEQ ID NO: 20 | YLGYLEQLLR | 1267.7051 | N.D. | N.D. |
| SEQ ID NO: 21 | VLYPNDNFFEGK | 1442.6957 | N.D. | N.D. |
| SEQ ID NO: 22 | LFTFHADICTLPDTEK | 1850.8999 | N.D. | N.D. |

Listed for each Q-peptide is the monoisotopic mass of the singly charged peptide (theoretical and measured) and the ppm difference.
[a] Q9 is present with a copy number of 3,
[b] Q10 with a copy number of 6.
N.D. - not detected.

Given the preferential detection of arginine-terminating tryptic peptides over their lysine-terminating counterparts by MALDI-ToF, PMF studies often benefit from being performed on tryptic peptides after conversion of lysine to homoarginine, thus improving peptide signal intensity (Brancia et al., 2000).

Figure 3:
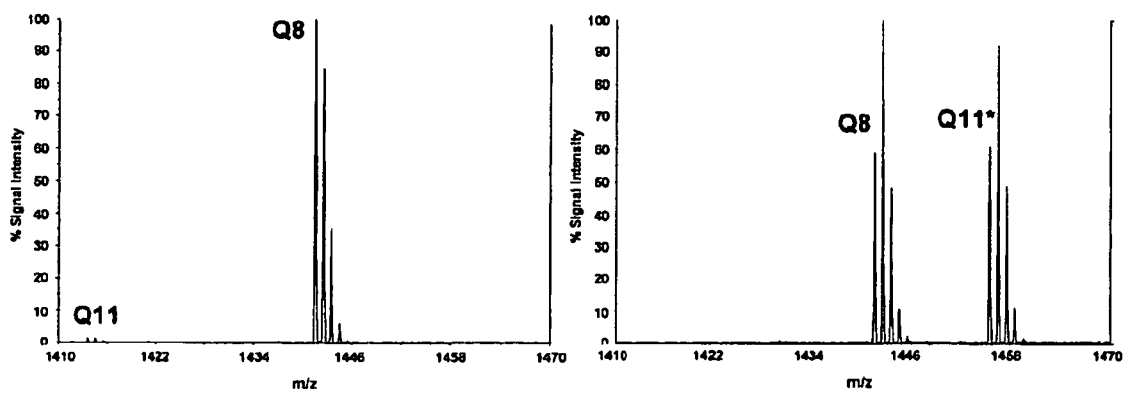
FIG. 3 shows the effect of guanidination on MALDI-ToF MS of Q8 and Q11. Trypsinised QCAL was analysed by MALDI-ToF MS before and after guanidination as described in the section "Examples". Depicted is m/z 1410-1470, clearly indicating preferential detection of the lysine-terminating Q11 peptide after guanidination (Q11*). Based on the change in isotope distribution post-guanidination, base catalysed deamidation of the peptides can also be observed as described in Song et al., 2001.

The almost identical Q-peptides 8 and 11 (FIG. 1A) were therefore specifically incorporated to test the efficiency of C-terminal homoarginine formation by lysine guanidination, with detection of Q11 only being possible after guanidination (FIG. 3).

High resolution mass spectrometers, such as the Fourier Transform Ion Cyclotron Resonance (FT ICR) and the orbitrap, which allow the determination of analyte masses to high accuracy (sub ppm mass difference), are becoming increasingly popular in proteomics applications, primarily due to the reduction in false positive peptide identification. Calibration of these instruments within the standard window for proteomics applications can be achieved using QCAL either as an external calibrant (FIG. 1C) (where average mass accuracy sub 1 ppm was achieved, and Table 2) or as an internal calibrant.

TABLE 2

Masses measured by FT ICR MS of trypsin digested QCAL

| Q-peptide | Sequence | Theoretical [M + H]⁺ | Measured [M + H]⁺ | Δppm | Theoretical [M + 2H]²⁺ | Measured [M + 2H]²⁺ | Δppm |
|---|---|---|---|---|---|---|---|
| SEQ ID NO: 1 | VFDEFKPLVEEPQNLIR | 2073.1021 | N.D. | N.D. | 1037.0550 | 1037.0548 | −0.18 |
| SEQ ID NO: 2 | VFDEFKPLVKPEEPQNLIR | 2298.2498 | N.D. | N.D. | 1149.6289 | 1149.6279 | −0.83 |
| SEQ ID NO: 3 | VFDEFKPLVKPEEKPQNLIR | 2426.3448 | N.D. | N.D. | 1213.6763 | 1213.6772 | 0.72 |
| SEQ ID NO: 4 | VFDEFKPLVKPEEKPQNKPLIR | 2651.4925 | N.D. | N.D. | 1326.2502 | N.D. | N.D. |
| SEQ ID NO: 5 | VFKPDEFKPLVKPEEKPQNKPLIR | 2876.6403 | N.D. | N.D. | 1438.8241 | N.D. | N.D. |
| SEQ ID NO: 6 | VFKPDEFKPLVKPEEKPQNKPLIKPR | 3101.7880 | N.D. | N.D. | 1551.3979 | N.D. | N.D. |
| SEQ ID NO: 7 | VFDEFQPLVEEPQNLIR | 2073.0657 | N.D. | N.D. | 1037.0368 | 1037.0368 | 0.00 |
| SEQ ID NO: 8 | GVNDNEEGFFSAR | 1441.6348 | 1441.6351 | 0.18 | 721.3214 | 721.3216 | 0.35 |
| SEQ ID NO: 9 | GGVNDNEEGFFSAR[a] | 1498.6563 | 1498.6585 | 1.47 | 749.8321 | 749.8312 | −1.19 |
| SEQ ID NO: 10 | GGGVNDNEEGFFSAR[b] | 1555.6778 | 1555.6769 | −0.55 | 778.3428 | 778.3421 | −0.93 |
| SEQ ID NO: 11 | GVNDNEEGFFSAK | 1413.6287 | 1413.6310 | 1.63 | 707.3183 | 707.3185 | 0.31 |
| SEQ ID NO: 12 | AVMDDFAAFVEK | 1342.6354 | 1342.6350 | −0.27 | 671.8216 | 671.8206 | −1.50 |
| SEQ ID NO: 13 | AVMMDDFAAFVEK | 1473.6758 | 1473.6778 | 1.33 | 737.3419 | 737.3418 | −0.08 |
| SEQ ID NO: 14 | AVMMMDDFAAFVEK | 1604.7163 | 1604.7138 | −1.58 | 802.8821 | 802.8819 | −0.25 |

TABLE 2-continued

Masses measured by FT ICR MS of trypsin digested QCAL

| | | | | | | | |
|---|---|---|---|---|---|---|---|
| SEQ ID NO: 15 | GLVK | 416.2873 | N.D. | N.D. | 208.6476 | N.D. | N.D. |
| SEQ ID NO: 16 | FVVPR | 617.3776 | 617.3763 | -2.02 | 309.1927 | N.D. | N.D. |
| SEQ ID NO: 17 | ALELFR | 748.4358 | 748.4358 | 0.01 | 374.7218 | N.D. | N.D. |
| SEQ ID NO: 18 | IGDYAGIK | 836.4518 | N.D. | N.D. | 418.7299 | N.D. | N.D. |
| SEQ ID NO: 19 | EALDFFAR | 968.4842 | N.D. | N.D. | 484.7460 | N.D. | N.D. |
| SEQ ID NO: 20 | YLGYLEQLLR | 1267.7051 | N.D. | N.D. | 634.3565 | N.D. | N.D. |
| SEQ ID NO: 21 | VLYPNDNFFEGK | 1442.6957 | N.D. | N.D. | 721.8518 | N.D. | N.D. |
| SEQ ID NO: 22 | LFTFHADICTLPDTEK | 1850.8999 | N.D. | N.D. | 925.9539 | N.D. | N.D. |

| Q-peptide | Sequence | Theoretical $[M + 3H]^{3+}$ | Measured $[M + 3H]^{3+}$ | Δppm | Theoretical $[M + 4H]^{4+}$ | Measured $[M + 4H]^{4+}$ | Δppm |
|---|---|---|---|---|---|---|---|
| SEQ ID NO: 1 | VFDEFKPLVEEPQNLIR | 691.7060 | 691.7043 | -2.39 | | | |
| SEQ ID NO: 2 | VFDEFKPLVKPEEPQNLIR | 766.7552 | 766.7540 | -1.55 | 575.3184 | 575.3183 | -0.10 |
| SEQ ID NO: 3 | VFDEFKPLVKPEEKPQNLIR | 809.4535 | 809.4518 | -2.11 | 607.3421 | 607.3446 | 4.12 |
| SEQ ID NO: 4 | VFDEFKPLVKPEEKPQNKPLIR | 884.5028 | 884.5013 | -1.64 | 663.6290 | 663.6298 | 1.16 |
| SEQ ID NO: 5 | VFKPDEFKPLVKPEEKPQNKPLIR | 959.5520 | 959.5529 | 0.94 | 719.9160 | 719.914 | -2.72 |
| SEQ ID NO: 6 | VFKPDEFKPLVKPEEKPQNKPLIKPR | 1034.6012 | 1034.6025 | 1.22 | 776.2029 | 776.2035 | 0.77 |
| SEQ ID NO: 7 | VFDEFQPLVEEPQNLIR | | | | | | |
| SEQ ID NO: 8 | GVNDNEEGFFSAR | | | | | | |
| SEQ ID NO: 9 | GGVNDNEEGFFSAR[a] | | | | | | |
| SEQ ID NO: 10 | GGGVNDNEEGPFSAR[b] | | | | | | |
| SEQ ID NO: 11 | GVNDNEEGFFSAK | | | | | | |
| SEQ ID NO: 12 | AVMDDFAAFVEK | | | | | | |
| SEQ ID NO: 13 | AVMMDDFAAFVEK | | | | | | |
| SEQ ID NO: 14 | AVMMMDDFAAFVEK | | | | | | |
| SEQ ID NO: 15 | GLVK | | | | | | |
| SEQ ID NO: 16 | FVVPR | | | | | | |
| SEQ ID NO: 17 | ALELFR | | | | | | |
| SEQ ID NO: 18 | IGDYAGIK | | | | | | |
| SEQ ID NO: 19 | EALDFFAR | | | | | | |
| SEQ ID NO: 20 | YLGYLEQLLR | | | | | | |
| SEQ ID NO: 21 | VLYPNDNFFEGK | | | | | | |
| SEQ ID NO: 22 | LFTFHADICTLPDTEK | 617.6388 | N.D. | N.D. | | | |

Listed for each Q-peptide is the monoisotopic mass of the singly, doubly, triply and quadruply charged peptide where appropriate (theoretical and measured) and the ppm difference.
[a] Q9 is present with a copy number of 3,
[b] Q10 with a copy number of 6.
N.D. - not detected.

To test the resolving power of instruments such as these, QCAL was designed to incorporate peptides Q1 and Q7, with a lysine to glutamine substitution. This results in a difference of 0.0364 amu and distinguishing these two peptides requires instrument resolution in excess of 57,000, quite within the capabilities of both the mass spectrometers mentioned above. Data acquired on a 9.4T FT ICR instrument indicates that, as expected, these two peptides can be readily distinguished (FIG. 1D, top panel), with peak resolution in excess of 105,000 being achieved. Detection of both of these peptides can therefore be used as a benchmark for instrument resolution. In addition, deamidation of a number of tryptic peptides from QCAL was also observed, with detection of the deamidated form of $Q9^{2+}$ (FIG. 1D, bottom label) requiring an instrument resolution in excess of 94,000. Detection of these deamidated species can thus be used as an additional specification for standardising the performance of high resolution instruments.

Figure 2:
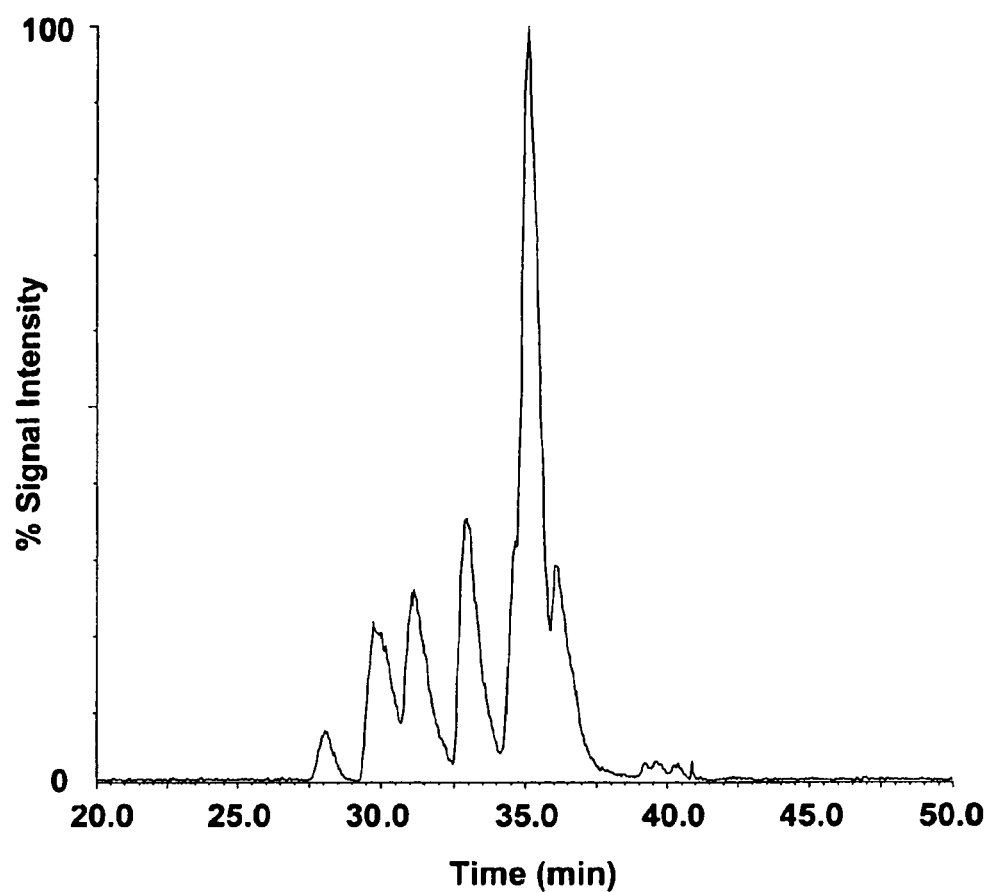
FIG. 2 shows the analysis of QCAL by LC-MS/MS. Tryptic peptides from QCAL (500 fmol) were separated by reversed-phase chromatography using a PepMap™ C18 columns (5 μm, 0.075×150 mm, 100 Å) from LC Packings. Chromatography was performed at 300 nl/min with bound peptides being eluted over a 30 min gradient from 90% A (1% MeCN, 0.1% FA), 10% B (50% MeCN, 0.1% FA) to 30% A, 70% B, arranged in-line with a QToF micro (Waters).
Figure 2:
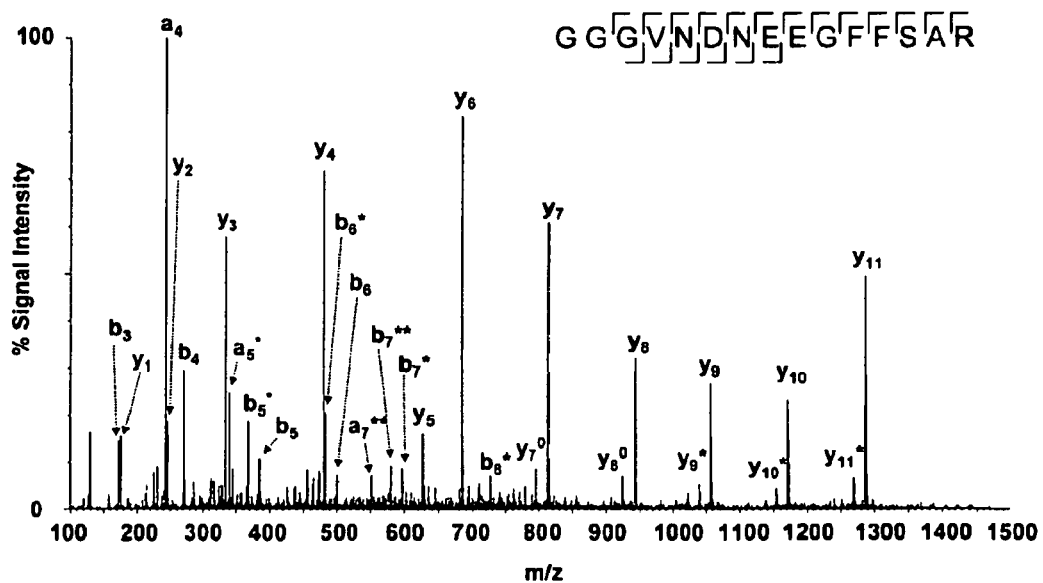
Figure 2:
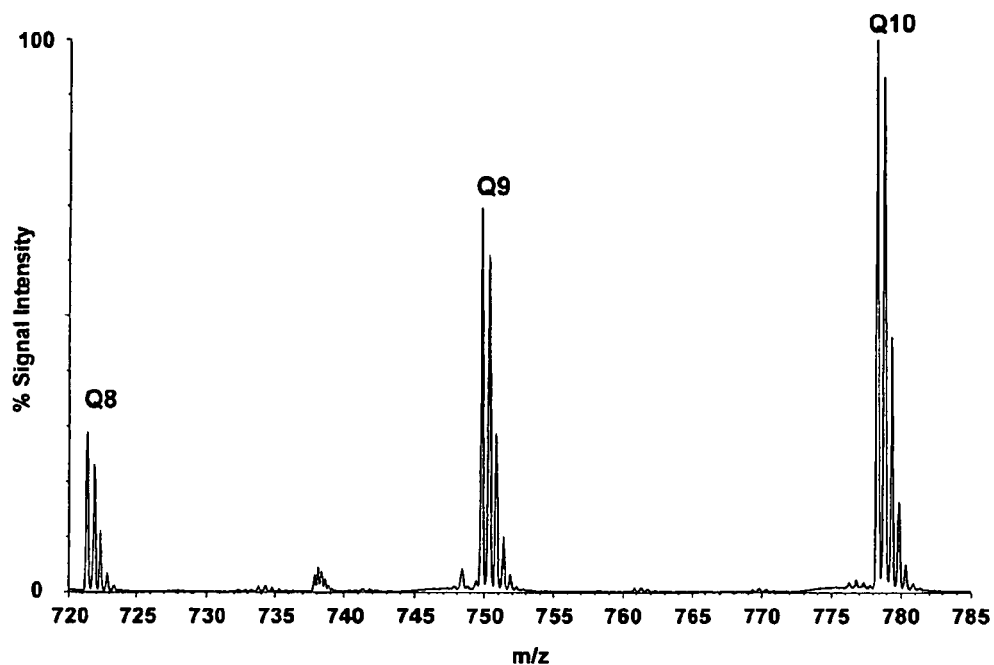

Critical to the success of proteomics experiments and the characterisation of peptides within complex mixtures is their separation by reversed-phase chromatography prior to mass spectrometric analysis. QCAL was therefore designed to incorporate peptides with a range of hydrophobicities, thereby permitting evaluation of reversed-phase chromatographic conditions for peptide separation. Reversed-phase chromatography of the QCAL tryptic peptides shows that they elute between 5 and ~35% acetonitrile (FIG. 2A and Table 3 below), the typical range over which most tryptic peptides elute from $C_{18}$ reversed-phase chromatographic media (Sun et al., 2004; Washburn, 2001).

into QCAL (Q8) to permit calibration post-fragmentation (FIG. 2B). Incorporation of Q8 also permits the testing of instrument sensitivity using the same configuration as is used for proteomics studies. This enables the end-user to optimise the position of the ionisation needle, thus maximising signal-to-noise detection for peptide analysis. The range of m/z and charge states of the peptides included in QCAL also permits optimisation of the rolling collision energy required to obtain high quality tandem MS spectra and thus the best possible peptide identification.

For quantification studies in particular, characterising the linearity of signal detection of the instrument is also critical. Multiple copies of two modified forms of the Glu-fibrinogen peptide, where one (Q9, three copies) or two (Q10, six copies) additional glycine residues have been added to the peptide

TABLE 3

| Q-peptide | Sequence | [M + H]$^+$ | Hopps-Wood Hydrophobicity | Elution time (min) |
|---|---|---|---|---|
| SEQ ID NO: 1 | VFDEFKPLVEEPQNLIR | 2073.1021 | 0.29 | 40.89 |
| SEQ ID NO: 2 | VFDEFKPLVKPEEPQNLIR | 2298.2498 | 0.42 | 39.21 |
| SEQ ID NO: 3 | VFDEFKPLVKPEEKPQNLIR | 2426.3448 | 0.55 | 36.01 |
| SEQ ID NO: 4 | VFDEFKPLVKPEEKPQNKPLIR | 2651.4925 | 0.64 | 32.94 |
| SEQ ID NO: 5 | VFKPDEFKPLVKPEEKPQNKPLIR | 2876.6403 | 0.71 | 31.15 |
| SEQ ID NO: 6 | VFKPDEFKPLVKPEEKPQNKPLIKPR | 3101.7880 | 0.77 | 29.95 |
| SEQ ID NO: 7 | VFDEFQPLVEEPQNLIR | 2073.0657 | 0.13 | 40.93 |
| SEQ ID NO: 8 | GVNDNEEGFFSAR | 1441.6348 | 0.44 | 35.52 |
| SEQ ID NO: 9 | GGVNDNEEGFFSAR[a] | 1498.6563 | 0.35 | 35.18 |
| SEQ ID NO: 10 | GGGVNDNEEGFFSAR[b] | 1555.6778 | 0.38 | 35.07 |
| SEQ ID NO: 11 | GVNDNEEGFFSAK | 1413.6287 | 0.44 | 34.64 |
| SEQ ID NO: 12 | AVMDDFAAFVEK | 1342.6354 | 0.10 | 41.02 |
| SEQ ID NO: 13 | AVMMDDFAAFVEK | 1473.6758 | −0.01 | 41.13 |
| SEQ ID NO: 14 | AVMMMDDFAAFVEK | 1604.7163 | −0.10 | 42.23 |
| SEQ ID NO: 15 | GLVK | 416.2873 | −0.08 | 29.75 |
| SEQ ID NO: 16 | FVVPR | 617.3776 | −0.50 | 28.06 |
| SEQ ID NO: 17 | ALELFR | 748.4358 | −0.10 | 36.29 |
| SEQ ID NO: 18 | IGDYAGIK | 836.4518 | −0.05 | 28.11 |
| SEQ ID NO: 19 | EALDFFAR | 968.4842 | 0.15 | 40.91 |
| SEQ ID NO: 20 | YLGYLEQLLR | 1267.7051 | −0.56 | N.D. |
| SEQ ID NO: 21 | VLYPNDNFFEGK | 1442.6957 | −0.10 | 39.64 |
| SEQ ID NO: 22 | LFTFHADICTLPDTEK | 1850.8999 | −0.10 | N.D. |

Listed for each Q-peptide is the Hopps-Wood hydrophobicity index, together with the elution time following reversed-phase chromatography.
N.D. - not detected.

A significant number of mass spectrometry laboratories use the Glu-fibrinogen peptide (GVNDNEEGFFSAR—SEQ ID NO: 8) for testing instrument sensitivity and also for calibration of the ToF following fragmentation. However, this sometimes requires a different instrument set-up (for example, analyte infusion) than is used for peptide analysis by LC-MS. This peptide sequence was therefore incorporated amino-terminus, were thus included in QCAL (FIG. 1A). Analysis of these three peptides by LC-MS on a quadrupole-time of flight (Q-ToF) instrument demonstrates that the additional glycine residues negatively affected peptide detection, with each additional glycine residue reducing peptide detection by ~15%. Instead of detecting a ratio of 1:3:6 for Q8:Q9:Q10, they were seen in a ratio of 1:2.6:3.9 (FIG. 2C). Similar changes in detection factors were also detected following LC-MS on a quadrupole ion trap (data not shown). However, MALDI-ToF analysis of these peptides (FIG. 1B) demonstrated a ratio of 1.0:3.4:6.0, closer to the actual peptide representation, indicating less glycine-dependent changes in peptide detection.

The data of this invention demonstrates that a single standard, QCAL, can be used for calibration and parameter optimisation of a number of instruments widely used in proteomics studies. Furthermore, it is believed that it will be possible to use this standard for testing and comparison in the development of new techniques and instruments for peptide analysis. More significantly, this standard will enable the proteomics community to define in more detail the behaviour of the instruments used in large-scale studies, thus facilitating long-term reproducibility in proteomics projects.

Examples

In the following, relevant methods for QCAL construction are described.

1. QCAL Construction.

Q-peptides were designed to assess mass spectrometer calibration and resolution, linearity of signal detection (by virtue of multiple copies of Q-peptides 9 and 10), peptide separation by reversed-phase chromatography and specific modifications incorporated during sample preparation: deamidation, modification of lysine, methionine and cysteine residues. The peptide sequences were then randomly concatenated in silico and used to direct the design of a gene, codon-optimised for expression in E. coli. The predicted transcript was subsequently analysed for RNA secondary structure that might diminish expression. Additional peptide sequences were added to provide an initiator methionine residue (MGALR—SEQ ID NO: 23), a $His_6$ sequence (ALVALVHHHHHH—SEQ ID NO: 24) for affinity purification using Ni-NTA resin and a sequence for removal of the tag with endoproteinases (ALVALV-LVPRGSLEVLFQGPIEGRTENLYFQGDDDDK—SEQ ID NO: 25). The gene was synthesised and cloned into the expression vector pET21a.

2. Expression and Sample Preparation.

QCAL was expressed and purified as previously described (Pratt et al., 2006), diluted to 1 mg/ml in 50 mM ammonium bicarbonate and digested with trypsin (2% (w/w), O/N). Digested QCAL (1 nmol) was dried by vacuum centrifugation and guanidination of lysine residues was performed by addition of ammonium hydroxide (7M, 10 μl) and O-methylisourea (0.5 M in water, 5 μl). After overnight incubation, samples were dried as above and desalted using C18 ZipTips (Millipore, Watford, UK) prior to MALDI-ToF analysis.

3. Fourier Transform Ion Cyclotron Resonance (FT ICR) Mass Spectrometry.

Digested QCAL was desalted using a $C_{18}$ peptide trap (Michrom Bioresources), dried by vacuum centrifugation and resuspended in 50% (v/v) acetonitrile, 0.1% (v/v) formic acid to 1 pmol/μl. The masses of the eluted pepetides were analysed using a Bruker Daltonics Apex III™ 9.4T FT ICR mass spectrometer (Billerica, Mass.) and an electrospray source, following infusion. Data acquisition was performed manually using the Bruker Xmass™ software, version 6.01 (Bruker Daltonics, Bremen, Germany). Mass spectra were collected using 512 data points per scan, over a mass range of 50-5000 m/z. High resolution data was collected over a mass range of 650-1500 m/z.

4. Matrix-Assisted Laser-Desorption Ionisation-Time of Flight (MALDI-ToF) Mass Spectrometry.

MALDI-ToF MS analysis was performed, using a Voyager-DE™ STR (Applied Biosystems) with digested QCAL crystallised with a saturated solution of alpha-cyanocinnamic acid in 50% (v/v) acetonitrile, 0.1% trifluoroacetic acid. Detection was performed in reflector mode with delayed extraction at 200 nsec.

REFERENCES

1. Beynon, R. J., Doherty, M. K., Pratt, J. M. & Gaskell, S. J. Multiplexed absolute quantification in proteomics using artificial QCAT proteins of concatenated signature peptides. Nat Methods 2, 587-9 (2005).
2. Brancia, F. L., Oliver, S. G. & Gaskell, S. J. Improved matrix-assisted laser desorption/ionization mass spectrometric analysis of tryptic hydrolysates of proteins following guanidination of lysine-containing peptides. Rapid Commun Mass Spectrom 14, 2070-3 (2000).
3. Cottrell, J. S. Protein identification by peptide mass fingerprinting. Pept Res 7, 115-24 (1994).
4. Pratt, J. M. et al. Multiplexed absolute quantification for proteomics using concatenated signature peptides encoded by QconCAT genes. Nat Protocols 1, 1029-43 (2006).
5. Song, Y., Schowen, R. L., Borchardt, R. T. & Topp, E. M. Effect of 'pH' on the rate of asparagine deamidation in polymeric formulations: 'pH'-rate profile. J Pharm Sci 90, 141-56 (2001).
6. Sun, W., Wu, S., Wang, X., Zheng, D. & Gao, Y. A systematical analysis of tryptic peptide identification with reverse phase liquid chromatography and electrospray ion trap mass spectrometry. Genomics Proteomics Bioinformatics 2, 174-83 (2004).
7. Washburn, M. P., Wolters, D. & Yates, J. R., 3rd. Large-scale analysis of the yeast proteome by multidimensional protein identification technology. Nat Biotechnol 19, 242-7 (2001).

The invention claimed is:

1. A polypeptide as standard for peptide analysis by mass spectrometry comprising at least 16 peptide sequences, at least 18 peptide sequences, at least 20 peptide sequences, or at least 22 peptide sequences selected from the group consisting of the peptide sequences VFDEFKPLVEEPQNLIR (SEQ ID NO: 1),
VFDEFKPLVKPEEPQNLIR (SEQ ID NO: 2),
VFDEFKPLVKPEEKPQNLIR (SEQ ID NO: 3),
FDEFKPLVKPEEKPQNKPLIR (SEQ ID NO: 4),
VFKPDEFKPLVKPEEKPQNKPLIR (SEQ ID NO: 5),
VFKPDEFKPLVKPEEKPQNKPLIKPR (SEQ ID NO: 6),
VFDEFQPLVEEPQNLIR (SEQ ID NO: 7),
GVNDNEEGFFSAR (SEQ ID NO: 8),
GGVNDNEEGFFSAR (SEQ ID NO: 9),
GGGVNDNEEGFFSAR (SEQ ID NO: 10),
GVNDNEEGFFSAK (SEQ ID NO: 11),
AVMDDFAAFVEK (SEQ ID NO: 12),
AVMMDDFAAFVEK (SEQ ID NO: 13),
AVMMMDDFAAFVEK (SEQ ID NO: 14),
GLVK (SEQ ID NO: 15),
FVVPR (SEQ ID NO: 16),
ALELFR (SEQ ID NO: 17),
IGDYAGIK (SEQ ID NO: 18),
EALDFFAR (SEQ ID NO: 19),
YLGYLEQLLR (SEQ ID NO: 20),
VLYPNDNFFEGK (SEQ ID NO: 21),
LFTFHADICTLPDTEK (SEQ ID NO: 22),
and/or functional variants thereof having conservative amino acid substitutions and/or substitution of aromatic amino acids with another aromatic amino acid.

2. The polypeptide of claim 1, wherein individual peptide sequences

VFDEFKPLVEEPQNLIR (SEQ ID NO: 1),
VFDEFKPLVKPEEPQNLIR (SEQ ID NO: 2),
VFDEFKPLVKPEEKPQNLIR (SEQ ID NO: 3),
FDEFKPLVKPEEKPQNKPLIR (SEQ ID NO: 4),
VFKPDEFKPLVKPEEKPQNKPLIR (SEQ ID NO: 5),
VFKPDEFKPLVKPEEKPQNKPLIKPR (SEQ ID NO: 6),
VFDEFQPLVEEPQNLIR (SEQ ID NO: 7),
GVNDNEEGFFSAR (SEQ ID NO: 8),
GGVNDNEEGFFSAR (SEQ ID NO: 9),
GGGVNDNEEGFFSAR (SEQ ID NO: 10),
GVNDNEEGFFSAK (SEQ ID NO: 11),
AVMDDFAAFVEK (SEQ ID NO: 12),
AVMMDDFAAFVEK (SEQ ID NO: 13),
AVMMMDDFAAFVEK (SEQ ID NO: 14),
GLVK (SEQ ID NO: 15),
FVVPR (SEQ ID NO: 16),
ALELFR (SEQ ID NO: 17),
IGDYAGIK (SEQ ID NO: 18),
EALDFFAR (SEQ ID NO: 19),
YLGYLEQLLR (SEQ ID NO: 20),
VLYPNDNFFEGK (SEQ ID NO: 21), and
LFTFHADICTLPDTEK (SEQ ID NO: 22)
are present more than one time in the polypeptide.

3. The polypeptide of claim 1, wherein the peptide sequence GGVNDNEEGFFSAR (SEQ ID NO: 9) is present up to five times in the polypeptide.

4. The polypeptide of claim 1, wherein the peptide sequence GGGVNDNEEGFFSAR (SEQ ID NO: 10) is present up to ten times in the polypeptide.

5. An artificial protein comprising the polypeptide of claim 1.

6. A vector comprising a nucleic acid encoding the polypeptide of claim 1.

7. A kit for proteome analysis comprising a polypeptide of claims 1 as standard for peptide analysis by mass spectrometry.

8. A method for calibration and evaluation of mass spectrometers and chromatographs for proteome analyses, the method comprising infusing the polypeptide of claim 1 into a mass spectrometer or chromatograph and evaluating the results of the infusion.

9. The polypeptide of claim 1, wherein the at least 22 peptide sequences comprises at least one peptide sequence, or a functional variant thereof having conservative amino acid substitutions and/or substitution of aromatic amino acids with another aromatic amino acid, of each of the peptide sequences VFDEFKPLVEEPQNLIR (SEQ ID NO: 1),
VFDEFKPLVKPEEPQNLIR (SEQ ID NO: 2),
VFDEFKPLVKPEEKPQNLIR (SEQ ID NO: 3),
FDEFKPLVKPEEKPQNKPLIR (SEQ ID NO: 4),
VFKPDEFKPLVKPEEKPQNKPLIR (SEQ ID NO: 5),
VFKPDEFKPLVKPEEKPQNKPLIKPR (SEQ ID NO: 6),
VFDEFQPLVEEPQNLIR (SEQ ID NO: 7),
GVNDNEEGFFSAR (SEQ ID NO: 8),
GGVNDNEEGFFSAR (SEQ ID NO: 9),
GGGVNDNEEGFFSAR (SEQ ID NO: 10),
GVNDNEEGFFSAK (SEQ ID NO: 11),
AVMDDFAAFVEK (SEQ ID NO: 12), AVMMDDFAAFVEK (SEQ ID NO: 13),
AVMMMDDFAAFVEK (SEQ ID NO: 14),
GLVK (SEQ ID NO: 15),
FVVPR (SEQ ID NO: 16),
ALELFR (SEQ ID NO: 17),
IGDYAGIK (SEQ ID NO: 18),
EALDFFAR (SEQ ID NO: 19),
YLGYLEQLLR (SEQ ID NO: 20),
VLYPNDNFFEGK (SEQ ID NO: 21), and
LFTFHADICTLPDTEK (SEQ ID NO: 22).

* * * * *

UNITED STATES PATENT AND TRADEMARK OFFICE
CERTIFICATE OF CORRECTION

PATENT NO. : 8,399,402 B2 Page 1 of 1
APPLICATION NO. : 12/599960
DATED : March 19, 2013
INVENTOR(S) : Beynon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 551 days.

Signed and Sealed this
First Day of September, 2015

Michelle K. Lee
*Director of the United States Patent and Trademark Office*

SEQUENCE LISTING

<160> NUMBER OF SEQ ID NOS: 25

<210> SEQ ID NO 1
<211> LENGTH: 17
<212> TYPE: PRT
<213> ORGANISM: Artificial
<220> FEATURE:
<223> OTHER INFORMATION: Tryptic peptide 1

<400> SEQUENCE: 1

```
Val Phe Asp Glu Phe Lys Pro Leu Val Glu Glu Pro Gln Asn Leu Ile
1               5                   10                  15

Arg

<210> SEQ ID NO 2
<211> LENGTH: 19
<212> TYPE: PRT
<213> ORGANISM: Artificial
<220> FEATURE:
<223> OTHER INFORMATION: Tryptic peptide 2

<400> SEQUENCE: 2

Val Phe Asp Glu Phe Lys Pro Leu Val Lys Pro Glu Glu Pro Gln Asn
1               5                   10                  15

Leu Ile Arg

<210> SEQ ID NO 3
<211> LENGTH: 20
<212> TYPE: PRT
<213> ORGANISM: Artificial
<220> FEATURE:
<223> OTHER INFORMATION: Tryptic peptide 3

<400> SEQUENCE: 3

Val Phe Asp Glu Phe Lys Pro Leu Val Lys Pro Glu Glu Lys Pro Gln
1               5                   10                  15

Asn Leu Ile Arg
            20

<210> SEQ ID NO 4
<211> LENGTH: 22
<212> TYPE: PRT
<213> ORGANISM: Artificial
<220> FEATURE:
<223> OTHER INFORMATION: Tryptic peptide 4

<400> SEQUENCE: 4

Val Phe Asp Glu Phe Lys Pro Leu Val Lys Pro Glu Glu Lys Pro Gln
1               5                   10                  15

Asn Lys Pro Leu Ile Arg
            20

<210> SEQ ID NO 5
<211> LENGTH: 24
<212> TYPE: PRT
<213> ORGANISM: Artificial
<220> FEATURE:
<223> OTHER INFORMATION: Tryptic peptide 5

<400> SEQUENCE: 5

Val Phe Lys Pro Asp Glu Phe Lys Pro Leu Val Lys Pro Glu Glu Lys
1               5                   10                  15

Pro Gln Asn Lys Pro Leu Ile Arg
            20

<210> SEQ ID NO 6
<211> LENGTH: 26
<212> TYPE: PRT
<213> ORGANISM: Artificial
<220> FEATURE:
<223> OTHER INFORMATION: Tryptic peptide 6

<400> SEQUENCE: 6

Val Phe Lys Pro Asp Glu Phe Lys Pro Leu Val Lys Pro Glu Glu Lys
```

```
1               5                  10                  15

Pro Gln Asn Lys Pro Leu Ile Lys Pro Arg
            20                  25

<210> SEQ ID NO 7
<211> LENGTH: 17
<212> TYPE: PRT
<213> ORGANISM: Artificial
<220> FEATURE:
<223> OTHER INFORMATION: Tryptic peptide 7

<400> SEQUENCE: 7

Val Phe Asp Glu Phe Gln Pro Leu Val Glu Glu Pro Gln Asn Leu Ile
1               5                  10                  15

Arg

<210> SEQ ID NO 8
<211> LENGTH: 13
<212> TYPE: PRT
<213> ORGANISM: Artificial
<220> FEATURE:
<223> OTHER INFORMATION: Tryptic peptide 8

<400> SEQUENCE: 8

Gly Val Asn Asp Asn Glu Glu Gly Phe Phe Ser Ala Arg
1               5                  10

<210> SEQ ID NO 9
<211> LENGTH: 14
<212> TYPE: PRT
<213> ORGANISM: Artificial
<220> FEATURE:
<223> OTHER INFORMATION: Tryptic peptide 9

<400> SEQUENCE: 9

Gly Gly Val Asn Asp Asn Glu Glu Gly Phe Phe Ser Ala Arg
1               5                  10

<210> SEQ ID NO 10
<211> LENGTH: 15
<212> TYPE: PRT
<213> ORGANISM: Artificial
<220> FEATURE:
<223> OTHER INFORMATION: Tryptic peptide 10

<400> SEQUENCE: 10

Gly Gly Gly Val Asn Asp Asn Glu Glu Gly Phe Phe Ser Ala Arg
1               5                  10                  15

<210> SEQ ID NO 11
<211> LENGTH: 13
<212> TYPE: PRT
<213> ORGANISM: Artificial
<220> FEATURE:
<223> OTHER INFORMATION: Tryptic peptide 11

<400> SEQUENCE: 11

Gly Val Asn Asp Asn Glu Glu Gly Phe Phe Ser Ala Lys
1               5                  10

<210> SEQ ID NO 12
<211> LENGTH: 12
<212> TYPE: PRT
<213> ORGANISM: Artificial
<220> FEATURE:
<223> OTHER INFORMATION: Tryptic peptide 12
```

```
<400> SEQUENCE: 12

Ala Val Met Asp Asp Phe Ala Ala Phe Val Glu Lys
1               5                   10

<210> SEQ ID NO 13
<211> LENGTH: 13
<212> TYPE: PRT
<213> ORGANISM: Artificial
<220> FEATURE:
<223> OTHER INFORMATION: Tryptic peptide 13

<400> SEQUENCE: 13

Ala Val Met Met Asp Asp Phe Ala Ala Phe Val Glu Lys
1               5                   10

<210> SEQ ID NO 14
<211> LENGTH: 14
<212> TYPE: PRT
<213> ORGANISM: Artificial
<220> FEATURE:
<223> OTHER INFORMATION: Tryptic peptide 14

<400> SEQUENCE: 14

Ala Val Met Met Met Asp Asp Phe Ala Ala Phe Val Glu Lys
1               5                   10

<210> SEQ ID NO 15
<211> LENGTH: 4
<212> TYPE: PRT
<213> ORGANISM: Artificial
<220> FEATURE:
<223> OTHER INFORMATION: Tryptic peptide 15

<400> SEQUENCE: 15

Gly Leu Val Lys
1

<210> SEQ ID NO 16
<211> LENGTH: 5
<212> TYPE: PRT
<213> ORGANISM: Artificial
<220> FEATURE:
<223> OTHER INFORMATION: Tryptic peptide 16

<400> SEQUENCE: 16

Phe Val Val Pro Arg
1               5

<210> SEQ ID NO 17
<211> LENGTH: 6
<212> TYPE: PRT
<213> ORGANISM: Artificial
<220> FEATURE:
<223> OTHER INFORMATION: Tryptic peptide 17

<400> SEQUENCE: 17

Ala Leu Glu Leu Phe Arg
1               5

<210> SEQ ID NO 18
<211> LENGTH: 8
<212> TYPE: PRT
<213> ORGANISM: Artificial
<220> FEATURE:
<223> OTHER INFORMATION: Tryptic peptide 18

<400> SEQUENCE: 18
```

```
Ile Gly Asp Tyr Ala Gly Ile Lys
1               5

<210> SEQ ID NO 19
<211> LENGTH: 8
<212> TYPE: PRT
<213> ORGANISM: Artificial
<220> FEATURE:
<223> OTHER INFORMATION: Tryptic peptide 19

<400> SEQUENCE: 19

Glu Ala Leu Asp Phe Phe Ala Arg
1               5

<210> SEQ ID NO 20
<211> LENGTH: 10
<212> TYPE: PRT
<213> ORGANISM: Artificial
<220> FEATURE:
<223> OTHER INFORMATION: Tryptic peptide 20

<400> SEQUENCE: 20

Tyr Leu Gly Tyr Leu Glu Gln Leu Leu Arg
1               5                   10

<210> SEQ ID NO 21
<211> LENGTH: 12
<212> TYPE: PRT
<213> ORGANISM: Artificial
<220> FEATURE:
<223> OTHER INFORMATION: Tryptic peptide 21

<400> SEQUENCE: 21

Val Leu Tyr Pro Asn Asp Asn Phe Phe Glu Gly Lys
1               5                   10

<210> SEQ ID NO 22
<211> LENGTH: 16
<212> TYPE: PRT
<213> ORGANISM: Artificial
<220> FEATURE:
<223> OTHER INFORMATION: Tryptic peptide 22

<400> SEQUENCE: 22

Leu Phe Thr Phe His Ala Asp Ile Cys Thr Leu Pro Asp Thr Glu Lys
1               5                   10                  15

<210> SEQ ID NO 23
<211> LENGTH: 5
<212> TYPE: PRT
<213> ORGANISM: Artificial
<220> FEATURE:
<223> OTHER INFORMATION: Initiator methionine residue

<400> SEQUENCE: 23

Met Gly Ala Leu Arg
1               5

<210> SEQ ID NO 24
<211> LENGTH: 12
<212> TYPE: PRT
<213> ORGANISM: Artificial
<220> FEATURE:
<223> OTHER INFORMATION: HIS-6 sequence

<400> SEQUENCE: 24

Ala Leu Val Ala Leu Val His His His His His His
1               5                   10
```

```
<210> SEQ ID NO 25
<211> LENGTH: 37
<212> TYPE: PRT
<213> ORGANISM: Artificial
<220> FEATURE:
<223> OTHER INFORMATION: Tag removal sequence

<400> SEQUENCE: 25

Ala Leu Val Ala Leu Val Leu Val Pro Arg Gly Ser Leu Glu Val Leu
1               5                   10                  15

Phe Gln Gly Pro Ile Glu Gly Arg Thr Glu Asn Leu Tyr Phe Gln Gly
                20                  25                  30

Asp Asp Asp Asp Lys
                35
```